(12) United States Patent
Park et al.

(10) Patent No.: US 9,523,117 B2
(45) Date of Patent: Dec. 20, 2016

(54) GENE ANALYSIS METHOD USING SDL-PCR

(75) Inventors: Hyun Gyu Park, Daejeon (KR); Sung Chul Shin, Daejeon (KR); Gahee Kim, Daejeon (KR); Byoung-Cheorl Kang, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 425 days.

(21) Appl. No.: 14/002,662

(22) PCT Filed: Jan. 30, 2012

(86) PCT No.: PCT/KR2012/000695
§ 371 (c)(1),
(2), (4) Date: Dec. 5, 2013

(87) PCT Pub. No.: WO2012/121486
PCT Pub. Date: Sep. 13, 2012

(65) Prior Publication Data
US 2014/0171334 A1 Jun. 19, 2014

(30) Foreign Application Priority Data

Mar. 4, 2011 (KR) .................. 10-2011-0019225

(51) Int. Cl.
*C12Q 1/68* (2006.01)

(52) U.S. Cl.
CPC ........... *C12Q 1/6853* (2013.01); *C12Q 1/6858* (2013.01)

(58) Field of Classification Search
None
See application file for complete search history.

(56) References Cited

U.S. PATENT DOCUMENTS

| 2003/0082584 A1 | 5/2003 | Shi et al. | |
|---|---|---|---|
| 2003/0108913 A1* | 6/2003 | Schouten | C12Q 1/686 435/6.18 |
| 2005/0266417 A1* | 12/2005 | Barany | C12Q 1/6827 435/6.12 |
| 2006/0088826 A1* | 4/2006 | Van Eijk | C12Q 1/6823 435/6.12 |
| 2007/0269805 A1* | 11/2007 | Hogers | C12Q 1/6827 435/6.12 |
| 2008/0051296 A1* | 2/2008 | Ginsberg | C12N 15/111 506/9 |
| 2010/0267585 A1 | 10/2010 | Terbrueggen | |
| 2011/0045462 A1* | 2/2011 | Fu | C12Q 1/6809 435/6.13 |
| 2011/0218115 A1 | 9/2011 | Chen et al. | |

FOREIGN PATENT DOCUMENTS

| WO | 2009140802 A1 | 11/2009 | |
|---|---|---|---|
| WO | WO 2011102802 A1 * | 8/2011 | ........... C12Q 1/6806 |

OTHER PUBLICATIONS

Ong et al. (Ligation with Nucleic Acid Sequence-Based Amplification, J Mol Diagn. May-Jun. 2012;14(3):206-13. Epub Mar. 23, 2012).*
Sobrino et al. (SNPs in forensic genetics: a review on SNP typing methodologies, Forensic Sci Int. Nov. 25, 2005;154(2-3):181-94. Epub Jan. 11, 2005).*
Asari, M., et al, "Enhanced discrimination of single nucleotide polymorphisms using 3'nucleotide differences in ligase detection reaction probes", "Molecular and Cellular Probes", Aug. 24, 2010, pp. 381-386, vol. 24.
Carnevale, E., et al., "A Multiplex Ligase Detection Reaction-Fluorescent Microsphere Assay for Simultaneous Detection of Single Nucleotide Polymorphisms Associated with Plasmodium falciparum Drug Resistance", "Journal of Clinical Microbiology", Mar. 2007, pp. 752-761, vol. 45, No. 3.
Hardenbol, P. et al., "Multiplexed genotyping with sequence-tagged molecular inversion probes", "Nature Biotechnology", Jun. 2003, pp. 673-678, vol. 21, No. 6.
Shen, R., et al, "High-throughput SNP genotyping on universal bead arrays", "Mutation Research", Feb. 2005, pp. 70-82, vol. 573.
Tobler, A., et al, "The SNPlex Genotyping System: A Flexible and Scalable Platform for SNP Genotyping", "Journal of Biomolecular Techniques", Dec. 2005, pp. 398-406, vol. 16, No. 4.

* cited by examiner

*Primary Examiner* — Aaron Priest
(74) *Attorney, Agent, or Firm* — Hultquist, PLLC; Steven J. Hultquist

(57) ABSTRACT

The present invention relates to a method for analyzing genes using SDL-PCR (separation of displaced ligation probe-based PCR), and more particularly to a method for analyzing genes using SDL-PCR, in which probes comprising a nucleotide sequence complementary to the gene of interest are ligated with each other by ligase, and another probe capable of hybridizing to the probes is hybridized and extended, thereby preparing a template probe, and the template probe for the gene of interest is amplified using universal primers.

According to the SDL-PCR method of the present invention, non-specific amplification can be minimized by removing non-ligated probes or genomic DNA using a tag, and separation can be achieved within a shorter time compared to a separation method that is performed using exonuclease. In addition, ligation, separation and polymerase chain reaction processes can be performed in a single solution in a single tube, and thus a plurality of genes can be amplified at the same time in an accurate and rapid manner.

13 Claims, 3 Drawing Sheets

GENE ANALYSIS METHOD USING SDL-PCR

TECHNICAL FIELD

The present invention relates to a method for analyzing genes using SDL-PCR (separation of displaced ligation probe-based PCR), and more particularly to a method for analyzing genes using SDL-PCR, in which probes comprising a nucleotide sequence complementary to the gene of interest are ligated with each other by ligase, and another probe capable of hybridizing to the probes is hybridized and extended, thereby preparing a template probe, and the template probe for the gene of interest is amplified using universal primers.

BACKGROUND ART

Methods that are most frequently used to obtain a gene sample for gene analysis include a polymerase chain reaction method based on DNA polymerase. This method has an advantage in that it can accurately amplify only the desired region of a desired gene by selectively controlling and designing the lengths and nucleotide sequences of primers capable of binding to the template DNA. However, in this method, only one gene of interest can be amplified by a single reaction, and thus when the number of the genes to be amplified is large, there is a shortcoming in that the same operation should be repeatedly performed.

To analyze a number of gene regions at the same time, a multiplex polymerase chain reaction method is widely used in which several polymerase chain reactions are performed in a single tube. However, in this method, a number of primers are simultaneously used in a single tube, and thus a cross-reaction between the primers occurs. For this reason, there is a shortcoming in that the number of gene regions that can be amplified at the same time is limited. In addition, there are shortcomings in that it requires large amounts of effort and time to find reaction conditions and in that good results in terms of sensitivity and specificity cannot be obtained (Hardenbol et al., *Nat. Biotechnol.*, 21:673, 2003).

In recent years, studies have been actively conducted to enable high-throughput analysis by amplifying a number of gene regions using universal primers without using multiplex polymerase chain reactions. Typical technologies include SNPlex capable of analyzing the single nucleotide polymorphisms (SNPs) of several gene regions at the same time, a Goldengate assay, molecular inversion probes (MIPs) and the like.

SNPlex is a method in which DNA is purified using exonuclease after an oligonucleotide ligation assay (OLA) and amplified by a polymerase chain reaction using universal primer nucleotide sequences located at both ends of the probe, after which the amplification products are analyzed in a DNA chip using a ZipCode nucleotide sequence included in the probe (Tobler et al., *J. Biomol. Tech.*, 16:398, 2005).

The Goldengate assay is a method in which an allele-specific primer extension reaction is performed on a genomic DNA immobilized on a solid surface using an upstream probe, after which the DNA is ligated with a downstream probe and washed to remove probes not ligated to the DNA. Then, the DNA is amplified using universal primer nucleotide sequences included in the probes, like the case of SNPlex, and the PCR amplification products are analyzed in Illumina BeadChip (Shen et al., *Mutat. Res.*, 573:70, 2005).

The molecular inversion probe (MIP) assay is a method in which gap-ligation is performed using a padlock probe, after which probes and genomic DNA, not ligated to the DNA, are removed using exonucelase, and the padlock probe is linearized using uracil-N-glycosylase. Then, the DNA is amplified by a polymerase chain reaction using universal primer nucleotide sequences included in the probe, and the amplification products are hybridized to the GenFlex tag array chip (Affymetrix) to analyze the single nucleotide polymorphisms (Hardenbol et al., *Nat. Biotechnol.*, 21:673, 2003).

However, these methods have problems in that, because portions of reaction products in a first tube are transferred and reacted in a second tube or several kinds of enzymes should be used, contamination between different samples can occur and experimental methods are complex.

Accordingly, the present inventors have made extensive efforts to solve the above-described problems occurring in the prior art, and as a result, have found that, when probes comprising a nucleotide sequence complementary to a gene of interest is ligated with each other by ligase and subjected to an extension reaction to prepare a template probe, which is then subjected to a separation process using a tag and amplified using universal primers, the template probe for the gene of interest can be amplified using the universal primers in a more accurate and rapid manner than conventional methods, thereby completing the present invention.

DISCLOSURE OF INVENTION

Technical Problem

It is an object of the present invention to provide a method for amplifying a gene using universal primers.

Another object of the present invention is to provide a method for detecting a plurality of genes using the above amplification method.

Still another object of the present invention is to provide a method for detecting mutations in a plurality of genes using the above amplification method.

Technical Solution

To achieve the above objects, the present invention provides an SDL-PCR method for amplifying a template probe for a gene of interest using universal primers, the method comprising the steps of: (a) preparing probe 1 including: a universal forward primer nucleotide sequence at the 5' end and including a nucleotide sequence complementary to a portion of a gene of interest; probe 2, the 5' end of which includes a nucleotide sequence complementary to a region following the gene portion for probe 1 and which includes an additional nucleotide sequence capable of hybridizing to probe 3; and probe 3 including a universal reverse primer nucleotide sequence and a nucleotide sequence complementary to the additional nucleotide sequence of probe 2; (b) mixing a mixture including the gene of interest with a mixture including probe 1 and probe 2, and adding ligase thereto to ligate probe 1 and probe 2 with each other; (c) adding probe 3, DNA polymerase and dNTP to the mixture resulting from step (b) to hybridize probe 3 to probe 2, and extending probe 3 so as to be complementary to the nucleotide sequences of probe 2 and probe 1, thereby preparing a template probe for the gene of interest, followed by separation of the template probe; and (d) amplifying the separated template probe of step (c) by a polymerase chain reaction (PCR) using the universal forward primer and the universal reverse primer.

The present invention also provides an SDL-PCR method for amplifying a template probe group for a plurality of genes of interest using universal primers, the method comprising the steps of: (a) preparing probe group 1 comprising a plurality of probes 1, which include a universal forward primer nucleotide sequence at the 5' end and each includes a nucleotide sequence complementary to a portion of each of a plurality of genes of interest; probe group 2 comprising a plurality of probes 2, the 5' end of each of which includes a nucleotide sequence complementary to a region following the gene portion for probes 1 and which include an additional nucleotide sequence capable of hybridizing to probe 3; and probe 3 including a universal reverse primer nucleotide sequence and a nucleotide sequence complementary to the additional nucleotide sequence of probes 2; (b) mixing a mixture including the plurality of genes of interest with a mixture including probe group 1 and probe group 2, and adding ligase thereto to ligate each probe 1 and each probe 2 with each other, which correspond to each of the plurality of genes of interest; (c) adding probe 3, DNA polymerase and dNTP to the mixture resulting from step (b) to hybridize probe 3 to each probe 2, and extending probe 3 so as to be complementary to the nucleotide sequences of probes 2 and probes 1, thereby preparing a template probe group including template probes for the plurality of genes of interest, followed by separation of the template probe group; and (d) amplifying the separated template probe group of step (c) by a polymerase chain reaction (PCR) using the universal forward primer and the universal reverse primer.

The present invention also provides a method for detecting a plurality of genes, the method comprising the steps of: (a) preparing and amplifying a template probe group for a plurality of genes of interest using the above SDL-PCR method; (b) modifying the amplification products into single strands; and (c) measuring the fluorescence of the modified amplification products to detect the presence or absence of the genes of interest.

The present invention also provides a method for detecting a plurality of genes, the method comprising the steps of: (a) amplifying a template probe group for a plurality of genes of interest by the above SDL-PCR method, in which probe 3 having varying lengths depending on the genes of interest is used; and (b) analyzing template probes for the genes of interest in the resulting amplification products using a mass spectrometer, and detecting the presence or absence of the genes of interest based on the presence or absence of peaks for the template probes.

The present invention also provides a method for detecting mutations in a plurality of genes, the method comprising the steps of: (a) preparing and amplifying a template probe group for a plurality of genes of interest using the above SDL-PCR method; (b) modifying the resulting amplification products into single strands; and (c) measuring the fluorescence of the modified amplification products to detect the presence or absence in mutations in the genes of interest.

BEST MODE FOR CARRYING OUT THE INVENTION

Figure 1:
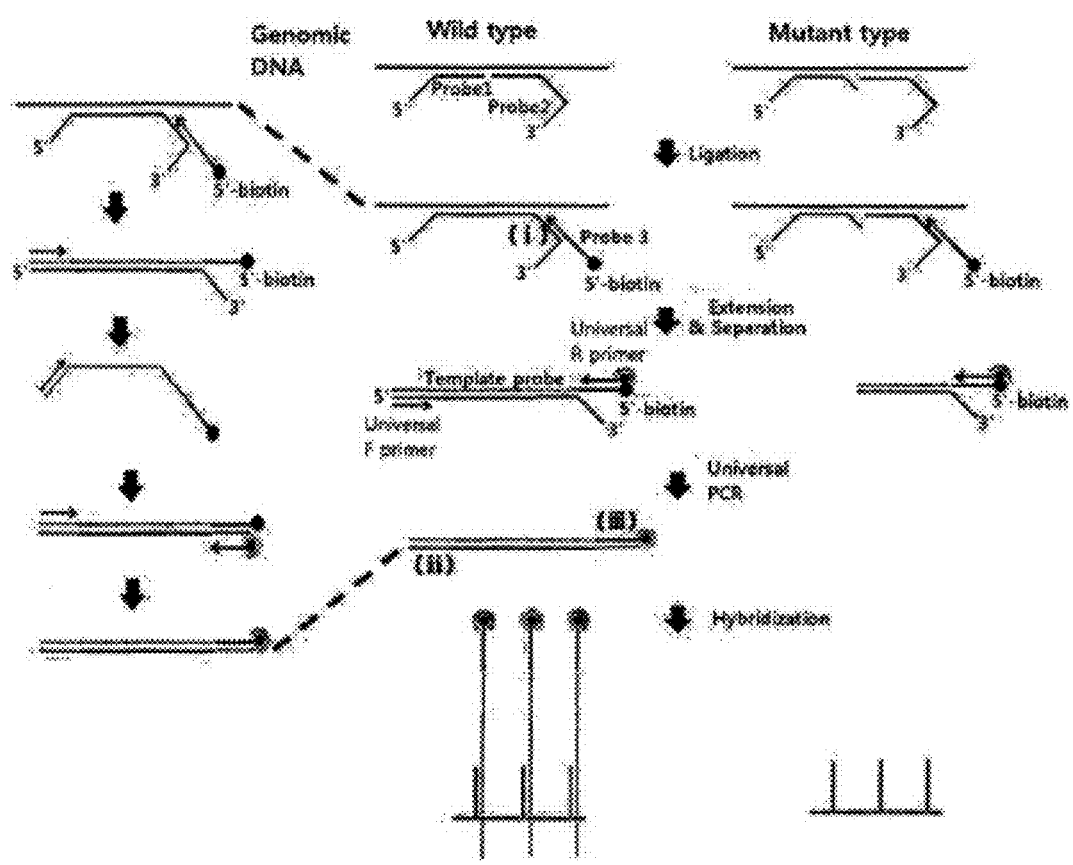
FIG. 1 shows the principle of SDL-PCR and the principle of a method for detecting gene mutations using a DNA chip.

As used herein, "SDL-PCR (separation of displaced ligation probe-based PCR)" refers to a method in which probes comprising nucleotide sequences complementary to portions of the gene of interest ligated using ligase and extended to prepare a template probe, which is then separated from unreacted probes, after which the template probe for the gene of interest is amplified using universal primers. More specifically, SDL-PCR refers to a method comprising: preparing a plurality of probes comprising a universal forward primer nucleotide sequence and each comprising a nucleotide sequence complementary to a portion of each of a plurality of genes of interest, and a plurality of probes 2, each of which comprises a nucleotide sequence complementary to a region following the gene portion included in the plurality of probes 1 and which comprise an additional nucleotide sequence capable of hybridizing to probe 3; ligating each probe 1 with each probe 2 using ligase; preparing probe 3 comprising a nucleotide sequence complementary to the additional nucleotide sequence of probes 2 and comprising a universal reverse primer nucleotide sequence; hybridizing probe 3 to the ligated probes; extending probe 3 so as to be complementary to the nucleotide sequences of the plurality of probes 2 and the plurality of probes 1, thereby preparing a plurality of template probes; performing a separation process to remove unreacted probes from the template probes; and simultaneously amplifying the plurality of template probes for the genes of interest using the universal forward primer and the universal reverse primer (see FIG. 1).

As used herein, "template probe" refers to a probe obtained by extending probe 3, which comprises a nucleotide sequence capable of hybridizing to probe 2 and includes a universal reverse primer sequence, so as to be complementary to the nucleotide sequences of probe 1 and probe 2. The template probe comprises a nucleotide sequence complementary to a universal forward primer at one end, a universal reverse primer nucleotide sequence at the other end, and a continuous nucleotide sequence complementary to portions of a gene of interest between both ends.

As used herein, the term "universal primer" refers to a primer that is universally used to amplify a plurality of genes in SDL-PCR of the present invention. The term "universal forward (F) primer" refers to the universal forward primer included in probe 1. Although the nucleotide sequence complementary to a portion of the gene of interest, which is included in probe 1, varies depending on the nucleotide sequence of the gene of interest, the universal forward primer nucleotide sequence does not vary depending on the gene of interest. As used herein, the term "universal reverse (R) primer" refers to the universal reverse primer included in probe 3, and the nucleotide sequence of the universal reverse primer does not vary depending on the gene of interest.

In one aspect, the present invention is directed to an SDL-PCR method for amplifying a template probe for a gene of interest using universal primers, the method comprising the steps of: (a) preparing probe 1 including: a universal forward primer nucleotide sequence at the 5' end and including a nucleotide sequence complementary to a portion of a gene of interest; probe 2, the 5' end of which includes a nucleotide sequence complementary to a region following the gene portion for probe 1 and which includes an additional nucleotide sequence capable of hybridizing to probe 3; and probe 3 including a universal reverse primer nucleotide sequence and a nucleotide sequence complementary to the additional nucleotide sequence of probe 2; (b) mixing a mixture including the gene of interest with a mixture including probe 1 and probe 2, and adding ligase thereto to ligate probe 1 and probe 2 with each other; (c) adding probe 3, DNA polymerase and dNTP to the mixture resulting from step (b) to hybridize probe 3 to probe 2, and extending probe 3 so as to be complementary to the nucleotide sequences of probe 2 and probe 1, thereby preparing a template probe for the gene of interest, followed by separation of the template probe; and (d) amplifying the separated template probe of step (c) by a polymerase chain reaction (PCR) using the universal forward primer and the universal reverse primer.

In another aspect, the present invention is directed to an SDL-PCR method for amplifying a template probe group for a plurality of genes of interest using universal primers, the method comprising the steps of: (a) preparing probe group 1 comprising a plurality of probes 1, which include a universal forward primer nucleotide sequence at the 5' end and each includes a nucleotide sequence complementary to a portion of each of a plurality of genes of interest; probe group 2 comprising a plurality of probes 2, the 5' end of each of which includes a nucleotide sequence complementary to a region following the gene portion for probes 1 and which include an additional nucleotide sequence capable of hybridizing to probe 3; and probe 3 including a universal reverse primer nucleotide sequence and a nucleotide sequence complementary to the additional nucleotide sequence of probes 2; (b) mixing a mixture including the plurality of genes of interest with a mixture including probe group 1 and probe group 2, and adding ligase thereto to ligate each probe 1 and each probe 2 with each other, which correspond to each of the plurality of genes of interest; (c) adding probe 3, DNA polymerase and dNTP to the mixture resulting from step (b) to hybridize probe 3 to each probe 2, and extending probe 3 so as to be complementary to the nucleotide sequences of probes 2 and probes 1, thereby preparing a template probe group including template probes for the plurality of genes of interest, followed by separation of the template probe group; and (d) amplifying the separated template probe group of step (c) by a polymerase chain reaction (PCR) using the universal forward primer and the universal reverse primer.

In the present invention, the ligase may be selected from the group consisting of 90N ligase, *E. coli* DNA ligase, Taq DNA ligase, T4 DNA ligase, and Ampligase ligase.

In the present invention, the DNA polymerase may be selected from the group consisting of Taq DNA polymerase and Pfu DNA polymerase, but is not limited thereto, and any thermostable DNA polymerase may be used.

In the present invention, probe 3 may further include a tag for separation at the 5' end, and the tag may be selected from the group consisting of biotin, avidin, streptavidin, antigens, antibodies, host compounds, guest compounds, metal chelate compounds, and nucleic acids.

In an example of the present invention, the 5' end of probe 3 was labeled with biotin, and separation of the template probe was performed using streptavidin-coated magnetic beads. However, separation of the template probe may also be performed by an antigen-antibody reaction, a metal chelating system based on a metal chelate compound, host-guest chemistry based on a host compound and a guest compound, or hybridization of nucleic acid.

In the present invention, the universal reverse primer may further comprise a fluorescent substance to determine the presence or absence of an amplification product, and the presence or absence of the amplification product may be determined using a DNA chip having a capture probe immobilized thereon.

The capture probe may include a nucleotide sequence complementary to a portion of the gene of interest to determine the presence or absence of the template probe for the gene of interest, and it may comprise a tag such as 5'-amine, 5'-thiol or 5'-biotin.

In still another aspect, the present invention is directed to a method for detecting a plurality of genes, the method comprising the steps of: (a) preparing and amplifying a template probe group for a plurality of genes of interest using the above SDL-PCR method; (b) modifying the amplification products into single strands; and (c) measuring the fluorescence of the modified amplification products to detect the presence or absence of the genes of interest.

In the present invention, the detection of the genes of interest may be performed using a DNA chip having capture probes immobilized thereon.

In yet another aspect, the present invention is directed to a method for detecting a plurality of genes, the method comprising the steps of: (a) amplifying a template probe group for a plurality of genes of interest by the above SDL-PCR method, in which probe 3 having varying lengths depending on the genes of interest is used; and (b) analyzing template probes for the genes of interest in the resulting amplification products using a mass spectrometer, and detecting the presence or absence of the genes of interest based on the presence or absence of peaks for the template probes.

In a further aspect, the present invention is directed to a method for detecting mutations in a plurality of genes, the method comprising the steps of: (a) preparing and amplifying a template probe group for a plurality of genes of interest using the above SDL-PCR method; (b) modifying the resulting amplification products into single strands; and (c) measuring the fluorescence of the modified amplification products to detect the presence or absence in mutations in the genes of interest.

In the present invention, the detection of mutations in the genes of interest may be performed using a DNA chip having capture probes immobilized thereon.

In an example of the present invention, as shown in FIG. 1, when the gene of interest to be amplified is a wild-type gene, probe 1 and probe 2 were prepared and ligated with each other by a DNA ligation reaction, and then probe 3 to be hybridized to portion (i) of probe 2 was prepared and added to a solution. An extension reaction was performed using a polymerase having displacement activity to prepare a template probe, which was then separated with streptavidin-coated magnetic beads using 5'-biotin of probe 3 to remove unligated probe 1 together with genomic DNA. This separation process significantly reduces non-specific amplification in a subsequent polymerase chain reaction that is performed using a single universal primer pair.

Subsequently, a polymerase chain reaction was performed using a universal forward (F) primer and a universal reverse (R) primer, which had portion (ii) of probe 1 and portion (iii) of probe 3, respectively, and then the resulting amplification product was hybridized to a DNA chip having immobilized thereon a capture probe for the gene of interest, and the fluorescence thereof was measured. As a result, it was shown that, in the case of the wild-type sample in which the DNA ligation reaction occurred, probe 3 was extended to the end of probe 1, suggesting that amplification occurred, whereas in the case of the mutant-type sample in which no DNA ligation reaction occurred, no PCR amplification occurred.

Figure 2:
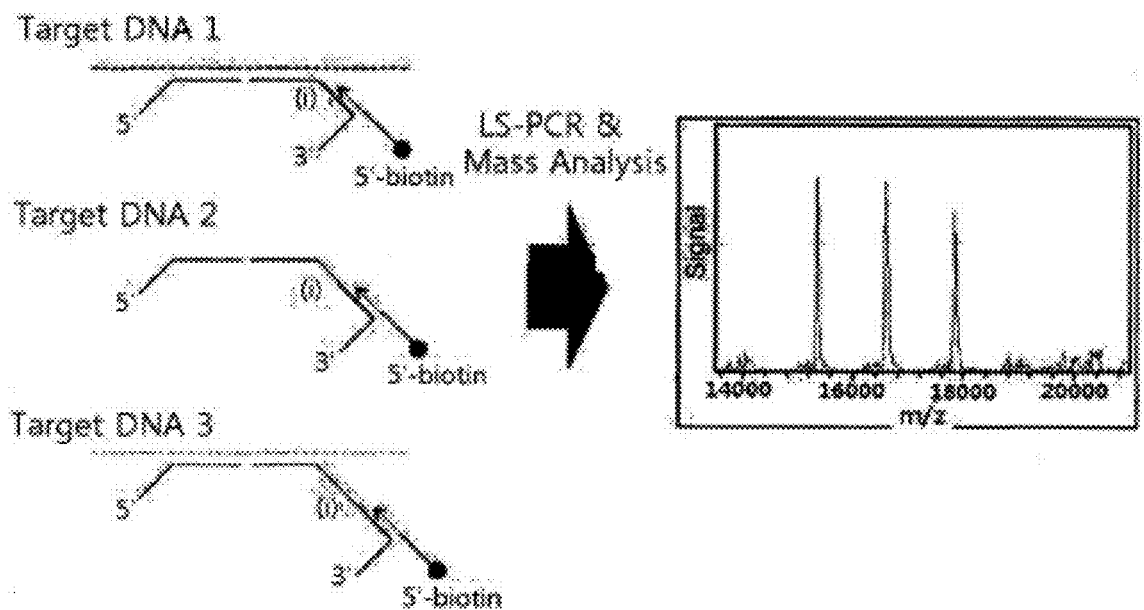
FIG. 2 shows the principle by which the presence or absence of target genes is determined using SDL-PCR and mass spectrometry.

FIG. 2 shows another method for detecting the presence or absence of target genes using SDL-PCR. As shown therein, SDL-PCR is performed using probes having different lengths of (i) portions for target genes, and then the presence or absence of the target genes can be determined using a mass spectrometer.

EXAMPLES

Hereinafter, the present invention will be described in further detail with reference to examples. It will be obvious to a person having ordinary skill in the art that these examples are illustrative purposes only and are not to be construed to limit the scope of the present invention.

Example

SDL-PCR Method 1-1: DNA Ligation Reaction

In order to perform SDL-PCR for four single nucleotide polymorphic sites, as shown in Table 1 below, probe 1, probe 2 and a capture probe for each of single nucleotide polymorphic sites of Pp6, Pp21, Pp28 and Pp99 were prepared and wild-type samples and mutant-type samples were prepared. In addition, a universal forward primer, a universal reverse primer and probe 3, which can be universally used for the four single nucleotide polymorphic sites, were prepared.

Probe 1 and probe 2 in the case of wild-type samples were prepared so that they were ligated with each other by a DNA ligation reaction. In addition, probe 1 was prepared so as to include a universal forward primer nucleotide sequence, and probe 2 was prepared so as to include a nucleotide sequence capable of hybridizing to probe 3 which can be universally used.

Probe 3 was prepared so as to include a nucleotide sequence capable of hybridizing to probe 2 and to include a universal reversal reverse primer nucleotide sequence which can be universally used. The 5' end of probe 3 was labeled with biotin for a separation reaction.

In addition, the 5' end of the universal reverse primer was labeled with Cy3 fluorescent dye in order to detect genes using a DNA chip.

TABLE 1

| Types | | | Nucleotide Sequences | SEQ ID NOS: |
|---|---|---|---|---|
| SDL Pp6 | | Probe 1 | TGT CTA TTG TTT GTG TGC TTG TTT T CGT TGA GGT CAT CGC | 1 |
| | | Probe 2 | CGG ACA GGA AGT CGT C AGT TGT TCA GTC TTA AAA AGG AGC C AAA AAA AAA AAA | 2 |
| | | Wild-type sample | AAA AAA AAA G ACG ACT TCC TGT CCG GCG ATG ACC TCA ACG AAA AAA AAA | 3 |
| | | Mutant-type sample | AAA AAA AAA G ACG ACT TCC TGT CCG ACG ATG ACC TCA ACG AAA AAA AAA | 4 |
| | | Capture Probe | AAA AAA AAA AAA CGT TGA GGT CAT CGC | 5 |
| SDL Pp21 | | Probe 1 | TGT CTA TTG TTT GTG TGC TTG TTT T CCT GTT CAA GTG ATC TTT TG | 6 |
| | | Probe 2 | TTC AAA TTT TGT GAT GAC C AGT TGT TCA GTC TTA AAA AGG AGC C AAA AAA AAA AAA | 7 |
| | | Wild-type sample | AAA AAA AAA G GTC ATC ACA AAA TTT GAA CA AAA GAT CAC TTG AAC AGG AAA AAA AAA | 8 |
| | | Mutant-type sample | AAA AAA AAA G GTC ATC ACA AAA TTT GAA AA AAA GAT CAC TTG AAC AGG AAA AAA AAA | 9 |
| | | Capture probe | AAA AAA AAA AAA CCT GTT CAA GTG ATC TTT TG | 10 |
| SDL Pp28 | | Probe 1 | TGT CTA TTG TTT GTG TGC TTG TTT T ATA ATT CTT GAT TTT AAA TCT CAA | 11 |
| | | Probe 2 | TCA GCA CGC CTA AGC AGT TGT TCA GTC TTA AAA AGG AGC C AAA AAA AAA AAA | 12 |
| | | Wild-type sample | AAA AAA AAA GCT TAG GCG TGC TGA TTG AGA TTT AAA ATC AAG AAT TAT AAA AAA AAA | 13 |

TABLE 1-continued

| Types | | Nucleotide Sequences | SEQ ID NOS: |
|---|---|---|---|
| | Mutant-type sample | AAA AAA AAA GCT TAG GCG TGC TGA CTG AGA TTT AAA ATC AAG AAT TAT AAA AAA AAA | 14 |
| | Capture probe | AAA AAA AAA AAA ATA ATT CTT GAT TTT AAA TCT CAA | 15 |
| SDL Pp99 | Probe 1 | TGT CTA TTG TTT GTG TGC TTG TTT T TCC TTT GTT TTT TAT GAT CTG | 16 |
| | Probe 2 | TTA ATT TGT GGC TCT GAC C AGT TGT TCA GTC TTA AAA AGG AGC C AAA AAA AAA AAA | 17 |
| | Wild-type sample | AAA AAA AAA G GTC AGA GCC ACA AAT TAA CAT ATC ATA AAA AAC AAA GGA AAA AAA AAA | 18 |
| | Mutant-type sample | AAA AAA AAA G GTC AGA GCC ACA AAT TAA GAT ATC ATA AAA AAC AAA GGA AAA AAA AAA | 19 |
| | Capture Probe | AAA AAA AAA AAA TCC TTT GTT TTT TAT GAT CTG | 20 |
| Universal Nucleotide Sequence | Universal F primer | TGT CTA TTG TTT GTG TGC TTG TTT T | 21 |
| | Universal R primer | GTG AAA AAT CCA AAT AAC CTT GAT G | 22 |
| | Probe 3 | GTG AAA AAT CCA AAT AAC CTT GAT G G GCT CCT TTT TAA GAC TGA | 23 |

Probe 1 and probe 2 for each of the prepared samples were diluted to 100 pM, and then 5 ul of each of probe 1 and probe 2 for each of Pp6, Pp21, Pp28 and Pp99 was mixed with 10 ul of distilled water, thereby preparing 50 ul of a DNA ligation probe mixture for each of Pp6, Pp21, Pp28 and Pp99.

Each of the prepared wild-type samples and mutant-type samples was diluted to 1 pM. In order to prepare a wild-type mixture for Pp6, 5 ul of a Pp6 wild-type sample was added to prepare 25 ul of a Pp6 wild-type mixture. In addition, 5 ul of each of Pp21, Pp28 and Pp99 mutant-type samples was added. Also, wild-type mixtures for Pp21, Pp28 and Pp99 were prepared in the same manner as described above.

In order to ligate probe 1 with probe 2, 5 ul of the Pp6 wild-type mixture, 10 ul of the DNA ligation probe mixture, 5 ul of 10×90N ligase buffer, 0.2 ul of 90N ligase (40 U/ul) and 29.8 ul of distilled water, and the mixture was allowed to react at 95° C. for 5 minutes, followed by reaction at 50° C. for 10 minutes, whereby probe 1 and probe 2 for Pp6 were ligated with each other. In the case of the wild-type mixtures for Pp21, Pp28 and Pp99, probe 1 and probe 2 were ligated with each other in the manner as described above.

1-2: DNA Extension Reaction and Separation Reaction

To each of the Pp6, Pp21, Pp28 and Pp99 wild-type mixtures containing probe 1 ligated to probe 2, 5 ul of 10 μM of probe 3, 5 ul of 10× ThermoPol buffer, 1 ul of 10 mM dNTP, 0.5 ul of Deep VentR™ DNA polymerase (2 U/ul) and 38.5 ul of distilled water were added. Each of the resulting mixtures was subjected to a DNA extension reaction at 55° C. for 5 minutes and at 72° C. for 30 seconds to hybridize probe 3 to probe 2 and to extend probe 3 to the end of probe 1.

To each of the DNA extension products that are template probes comprising probe that extended to probe 2 and probe 1, 1 ul of streptavidin-coated magnetic beads. Each of the resulting mixtures was vortexed and reacted at room temperature for 15 minutes, and then the magnetic beads were concentrated on one side using a magnet to remove the supernatant. Then, 50 ul of distilled water was added to each residue and mixed using a pipette, the magnetic beads were concentrated on one side using a magnetic to remove the supernatant, and this process was repeated twice. In this way, unreacted probe and sample DNA were removed from the template probes in which the DNA ligation reaction occurred.

This separation process can significantly reduce non-specific amplification in a polymerase chain reaction that is performed using a single universal primer pair.

1-3: Polymerase Chain Reaction (PCR) Using Universal Primers

To the magnetic beads having the separated template probes attached thereto for each of the Pp6, Pp21, Pp28 and Pp99 wild-type mixtures, 10 ul of 5× Phusion HF buffer, 1 ul of 10 mM dNTP, 5 ul of 5 uM universal forward primer, 5 ul of 5 uM universal reverse primer, 0.5 ul of Phusion Hot Start II High-Fidelity DNA polymerase and 27.5 ul of distilled water were added, and the resulting mixtures were subjected to PCR under the following conditions: initial denaturation at 98° C. for 2 min, then 34 cycles of 10 sec at 98, 20 sec at 60° C. and 30 sec at 72° C., followed by final extension at 72° C. for 5 min.

1-4: Analysis of Amplification Products Using DNA Chip

To analyze the amplification products for Pp6, Pp21, Pp28 and Pp99, the amplification products obtained in Example 1-3 were purified using NucleoSpin® Extract II kit (MA-CHEREY-NAGEL). More specifically, according to a common purification protocol, each of the amplification products was mixed with binding buffer and bound to the NucleoSpin® Extract II column, after which it was washed with washing buffer and eluted with distilled water.

Meanwhile, to prepare a slide having a capture probe immobilized thereon, a capture probe tagged with 5'-amine was spotted on an epoxy-coated glass slide (Luminano) using a microarrayer (Bio-Rad) and reacted overnight, and then the slide was washed with 0.2% SDS and then with distilled water, thereby preparing a slide having the capture probe immobilized thereon.

Each of the purified amplification products was heated at 95° C. for 10 minutes and incubated at −20° C. for 10 minutes, and then 30 ul of each amplification product was immediately mixed with 30 ul of 2×SSPE (0.9M NaCl, 60 mM NaH2PO4, 6 mM EDTA, pH 7.4) buffer and placed on the slide glass having the capture probe immobilized thereon, followed by hybridization at 37° C. for 4 hours. Each slide glass was washed with washing buffer (6×SSPE with 0.005% Triton X-100) for 10 minutes and with distilled water for 10 minutes and dried, after each slide glass was scanned with a fluorescence scanner (Axon scanner 4000A) using a Cy3 fluorescent dye labeled on the universal reverse primer.

Figure 3:
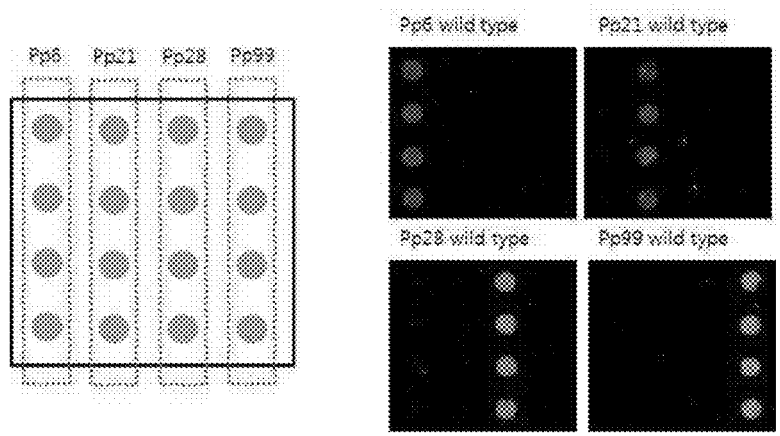
FIG. 3 shows the results obtained by performing SDL-PCR on single nucleotide polymorphic sites of Pp6, Pp21, Pp28 and Pp99, and then applying the amplification products to a DNA chip to measure the fluorescence of the amplification products.

As a result, as shown in FIG. 3, in the case of the Pp6 wild-type mixture, a fluorescence signal appeared only at the Pp6 capture probe, and in the case of the Pp21, Pp28 and Pp99 wild-type mixtures, fluorescence appeared only at each wild-type capture probe.

This suggests that genotypes for a number of single nucleotide polymorphic sites can be analyzed using SDL-PCR.

In addition, SDL-PCR was performed on each of the wide-type samples and the mutant-type samples, and the amplification products were analyzed by 2% agarose gel electrophoresis.

Figure 4:
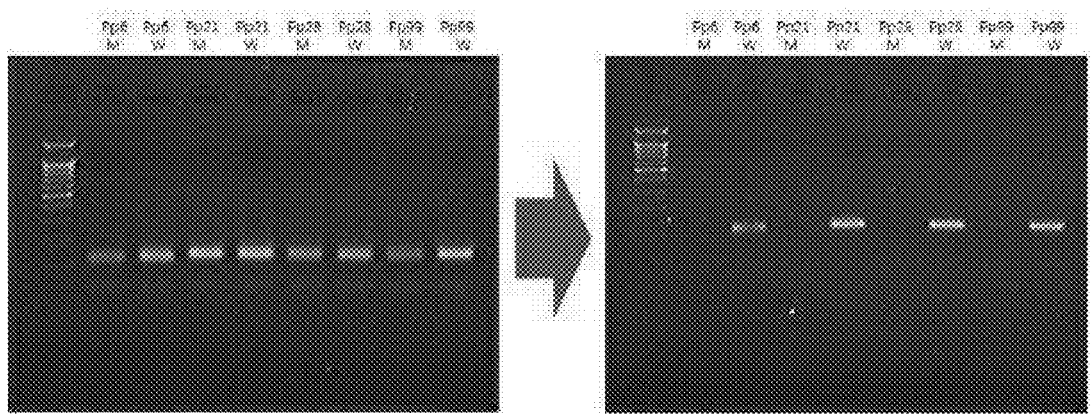
FIG. 4 shows the results of electrophoresis of non-separated SDL-PCR amplification products (left) and separated SDL-PCR amplification products (right) for wild-type samples (W) and mutant-type samples (M).

As a result, as shown in FIG. 4, in the case of the samples which were not subjected to the separation process, non-specific amplification occurred even in the mutant-type samples, and thus bands appeared in all the wild-type samples and the mutant-type samples, whereas in the case of the samples which were subjected to the separation process, bands appeared only in the wild-type samples.

Such results suggest that non-specific amplification can be reduced by the separation process, and thus SDL-PCR can be applied to determine whether a specific single nucleotide polymorphic marker for the genomic DNA to be analyzed is wild-type or mutant-type.

INDUSTRIAL APPLICABILITY

According to the SDL-PCR method of the present invention, non-specific amplification can be minimized by removing non-ligated probes or genomic DNA using a tag, and separation can be achieved within a shorter time compared to a separation method that is performed using exonuclease. In addition, ligation, separation and polymerase chain reaction processes can be performed in a single solution in a single tube, and thus a plurality of genes can be amplified at the same time in an accurate and rapid manner.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

Sequence List (Free Text)
Attach electric file.

The invention claimed is:

1. An SDL-PCR method for amplifying a template probe for a gene of interest using universal primers, the method comprising the steps of:
   (a) mixing a mixture including the gene of interest with a mixture including probe 1 and probe 2, and adding ligase thereto to ligate probe 1 and probe 2 with each other;
   (b) adding probe 3, DNA polymerase and dNTP to the mixture resulting from step (b) to hybridize probe 3 to probe 2, and extending probe 3 so as to be complementary to the nucleotide sequences of probe 2 and probe 1, thereby preparing a template probe for the gene of interest;
   (c) separating the template probe using a tag; and
   (d) amplifying the separated template probe of step (c) by a polymerase chain reaction (PCR) using a primer pair corresponding to a universal forward primer nucleotide sequence and a universal reverse primer nucleotide sequence,
   wherein the probe 1 includes, from 5' direction to 3' direction, the following: a universal forward primer nucleotide sequence and a nucleotide sequence complementary to a portion of a gene of interest,
   wherein the probe 2 includes, from 5' direction to 3' direction, the following: a nucleotide sequence complementary to a 5' to 3' region following the portion of a gene of interest of probe 1 and an additional nucleotide sequence which hybridizes to probe 3,
   wherein the probe 3 includes, from 3' direction to 5' direction, the following: a nucleotide sequence complementary to the additional nucleotide sequence of probe 2, a universal reverse primer nucleotide sequence, and a tag for separation,
   wherein the universal reverse primer nucleotide sequence and the nucleotide sequence complementary to the additional nucleotide sequence of probe 2 are different,
   wherein the tag is selected from the group consisting of biotin, avidin, streptavidin, antigens, antibodies, host compounds, guest compounds, metal chelate compounds, and nucleic acids, and
   wherein the primer corresponding to the universal reverse primer nucleotide sequence further comprises a fluorescent substance to determine the presence or absence of an amplification product.

2. The SDL-PCR method of claim 1, wherein the ligase is selected from the group consisting of *E. coli* DNA ligase, Taq DNA ligase, and T4 DNA ligase.

3. The SDL-PCR method of claim 1, wherein the DNA polymerase is selected from the group consisting of Taq DNA polymerase and Pfu DNA polymerase.

4. The SDL-PCR method of claim 1, wherein the presence or absence of the amplification product is determined using a DNA chip having a capture probe immobilized thereon.

5. An SDL-PCR method for amplifying a template probe group for a plurality of genes of interest using universal primers, the method comprising the steps of:
   (a) mixing a mixture including the plurality of genes of interest with a mixture including probe group 1 and probe group 2, and adding ligase thereto to ligate each probe 1 and each probe 2 with each other, which correspond to each of the plurality of genes of interest;
   (b) adding probe 3, DNA polymerase and dNTP to the mixture resulting from step (a) to hybridize probe 3 to each probe 2, and extending probe 3 so as to be complementary to the nucleotide sequences of probes 2 and probes 1, thereby preparing a template probe group including template probes for the plurality of genes of interest,
   (c) separating the template probe using a tag; and
   (d) amplifying the separated template probe of step (c) by a polymerase chain reaction (PCR) using a primer pair corresponding to a universal forward primer nucleotide sequence and a universal reverse primer nucleotide sequence,
   wherein the probe group 1 comprises a plurality of probes 1, each of which include from 5' direction to 3' direction, the following: a universal forward primer nucleotide sequence and a nucleotide sequence complementary to a portion of a gene of interest,
   wherein the probe group 2 comprises a plurality of probes 2, each of which include from 5' direction to 3' direction, the following: a nucleotide sequence complementary to a 5' to 3' region following the portion of a gene of interest of probe 1 and an additional nucleotide sequence which hybridizes to probe 3,
   wherein the probe 3 includes, from 3' direction to 5' direction, the following: a nucleotide sequence complementary to the additional nucleotide sequence of probe 2, a universal reverse primer nucleotide sequence, and a tag for separation,
   wherein the universal reverse primer nucleotide sequence and the nucleotide sequence complementary to the additional nucleotide sequence of probe 2 are different,
   wherein the tag is selected from the group consisting of biotin, avidin, streptavidin, antigens, antibodies, host compounds, guest compounds, metal chelate compounds, and nucleic acids, and
   wherein the primer corresponding to the universal reverse primer nucleotide sequence further comprises a fluorescent substance to determine the presence or absence of an amplification product.

6. The SDL-PCR method of claim 5, wherein the ligase is selected from the group consisting of *E. coli* DNA ligase, Taq DNA ligase, T4 DNA ligase.

7. The SDL-PCR method of claim 5, wherein the DNA polymerase is selected from the group consisting of Taq DNA polymerase and Pfu DNA polymerase.

8. The SDL-PCR method of claim 5, wherein the presence or absence of the amplification product is determined using a DNA chip having a capture probe immobilized thereon.

9. A method for detecting a plurality of genes, the method comprising the steps of:

(a) preparing and amplifying a template probe group for a plurality of genes of interest using the SDL-PCR method of claim 5;
(b) modifying the amplification products into single strands; and
(c) measuring the fluorescence of the modified amplification products to detect the presence or absence of the genes of interest.

10. The method of claim 9, wherein the detection of the genes of interest is performed using a DNA chip having capture probes immobilized thereon.

11. A method for detecting a plurality of genes, the method comprising the steps of:
(a) amplifying a template probe group for a plurality of genes of interest by the SDL-PCR method of claim 8, in which probe 3 having varying lengths depending on the genes of interest is used; and
(b) analyzing template probes for the genes of interest in the resulting amplification products using a mass spectrometer, and detecting the presence or absence of the genes of interest based on the presence or absence of peaks for the template probes.

12. A method for detecting mutations in a plurality of genes, the method comprising the steps of:
(a) preparing and amplifying a template probe group for a plurality of genes of interest using the SDL-PCR method of claim 5;
(b) modifying the resulting amplification products into single strands; and
(c) measuring the fluorescence of the modified amplification products to detect the presence or absence in mutations in the genes of interest.

13. The method of claim 12, wherein the detection of mutations in the genes of interest is performed using a DNA chip having capture probes immobilized thereon.

* * * * *

UNITED STATES PATENT AND TRADEMARK OFFICE
CERTIFICATE OF CORRECTION

PATENT NO. : 9,523,117 B2
APPLICATION NO. : 14/002662
DATED : December 20, 2016
INVENTOR(S) : Hyun Gyu Park et al.

Page 1 of 1

It is certified that error appears in the above-identified patent and that said Letters Patent is hereby corrected as shown below:

On the Title Page

Under (75) Inventors: "Byoung-Cheorl Kang" should be --Vyoung-Cheorl Kang--;

In the Specification

Column 9, Line 60: "5 ul of 10 µM" should be --5 ul of 10 pM--.

Signed and Sealed this
Seventh Day of March, 2017

Michelle K. Lee
*Director of the United States Patent and Trademark Office*

SEQUENCE LISTING

```
<160> NUMBER OF SEQ ID NOS: 23

<210> SEQ ID NO 1
<211> LENGTH: 40
<212> TYPE: DNA
<213> ORGANISM: Artificial
<220> FEATURE:
<223> OTHER INFORMATION: SDL Pp6 probe 1

<400> SEQUENCE: 1
tgtctattgt ttgtgtgctt gttttcgttg aggtcatcgc                40

<210> SEQ ID NO 2
<211> LENGTH: 53
<212> TYPE: DNA
<213> ORGANISM: Artificial
<220> FEATURE:
<223> OTHER INFORMATION: SDL Pp6 probe 2

<400> SEQUENCE: 2
cggacaggaa gtcgtcagtt gttcagtctt aaaaaggagc caaaaaaaaa aaa       53

<210> SEQ ID NO 3
<211> LENGTH: 49
<212> TYPE: DNA
<213> ORGANISM: Artificial
<220> FEATURE:
<223> OTHER INFORMATION: SDL Pp6 wild type sample
```

```
<400> SEQUENCE: 3
aaaaaaaaag acgacttcct gtccggcgat gacctcaacg aaaaaaaaa          49

<210> SEQ ID NO 4
<211> LENGTH: 49
<212> TYPE: DNA
<213> ORGANISM: Artificial
<220> FEATURE:
<223> OTHER INFORMATION: SDL Pp6 mutant type sample

<400> SEQUENCE: 4
aaaaaaaaag acgacttcct gtccgacgat gacctcaacg aaaaaaaaa          49

<210> SEQ ID NO 5
<211> LENGTH: 27
<212> TYPE: DNA
<213> ORGANISM: Artificial
<220> FEATURE:
<223> OTHER INFORMATION: SDL Pp6 capture probe

<400> SEQUENCE: 5
aaaaaaaaaa aacgttgagg tcatcgc                                  27

<210> SEQ ID NO 6
<211> LENGTH: 45
<212> TYPE: DNA
<213> ORGANISM: Artificial
<220> FEATURE:
<223> OTHER INFORMATION: SDL Pp21 probe 1

<400> SEQUENCE: 6
tgtctattgt ttgtgtgctt gttttcctgt tcaagtgatc ttttg              45

<210> SEQ ID NO 7
<211> LENGTH: 56
<212> TYPE: DNA
<213> ORGANISM: Artificial
<220> FEATURE:
<223> OTHER INFORMATION: SDL Pp21 probe 2

<400> SEQUENCE: 7
ttcaaatttt gtgatgacca gttgttcagt cttaaaaagg agccaaaaaa aaaaaa   56

<210> SEQ ID NO 8
<211> LENGTH: 57
<212> TYPE: DNA
<213> ORGANISM: Artificial
<220> FEATURE:
<223> OTHER INFORMATION: SDL Pp21 wild type sample

<400> SEQUENCE: 8
aaaaaaaaag gtcatcacaa aatttgaaca aaagatcact tgaacaggaa aaaaaaa  57

<210> SEQ ID NO 9
<211> LENGTH: 57
<212> TYPE: DNA
<213> ORGANISM: Artificial
<220> FEATURE:
<223> OTHER INFORMATION: SDL Pp21 mutant type sample

<400> SEQUENCE: 9
aaaaaaaaag gtcatcacaa aatttgaaaa aaagatcact tgaacaggaa aaaaaaa  57

<210> SEQ ID NO 10
<211> LENGTH: 32
```

```
<212> TYPE: DNA
<213> ORGANISM: Artificial
<220> FEATURE:
<223> OTHER INFORMATION: SDL Pp21 capture probe

<400> SEQUENCE: 10
aaaaaaaaaa aacctgttca agtgatcttt tg                                  32

<210> SEQ ID NO 11
<211> LENGTH: 49
<212> TYPE: DNA
<213> ORGANISM: Artificial
<220> FEATURE:
<223> OTHER INFORMATION: SDL Pp28 probe 1

<400> SEQUENCE: 11
tgtctattgt ttgtgtgctt gttttataat tcttgatttt aaatctcaa              49

<210> SEQ ID NO 12
<211> LENGTH: 52
<212> TYPE: DNA
<213> ORGANISM: Artificial
<220> FEATURE:
<223> OTHER INFORMATION: SDL Pp28 probe 2

<400> SEQUENCE: 12
tcagcacgcc taagcagttg ttcagtctta aaaggagcc aaaaaaaaaa aa            52

<210> SEQ ID NO 13
<211> LENGTH: 57
<212> TYPE: DNA
<213> ORGANISM: Artificial
<220> FEATURE:
<223> OTHER INFORMATION: SDL Pp28 wild type sample

<400> SEQUENCE: 13
aaaaaaaaag cttaggcgtg ctgattgaga tttaaaatca agaattataa aaaaaaa      57

<210> SEQ ID NO 14
<211> LENGTH: 57
<212> TYPE: DNA
<213> ORGANISM: Artificial
<220> FEATURE:
<223> OTHER INFORMATION: SDL Pp28 mutant type sample

<400> SEQUENCE: 14
aaaaaaaaag cttaggcgtg ctgactgaga tttaaaatca agaattataa aaaaaaa      57

<210> SEQ ID NO 15
<211> LENGTH: 36
<212> TYPE: DNA
<213> ORGANISM: Artificial
<220> FEATURE:
<223> OTHER INFORMATION: SDL Pp28 capture probe

<400> SEQUENCE: 15
aaaaaaaaaa aaataattct tgattttaaa tctcaa                              36

<210> SEQ ID NO 16
<211> LENGTH: 46
<212> TYPE: DNA
<213> ORGANISM: Artificial
<220> FEATURE:
<223> OTHER INFORMATION: SDL Pp99 probe 1

<400> SEQUENCE: 16
```

```
tgtctattgt ttgtgtgctt gttttcctt tgttttttat gatctg         46
```

<210> SEQ ID NO 17
<211> LENGTH: 56
<212> TYPE: DNA
<213> ORGANISM: Artificial
<220> FEATURE:
<223> OTHER INFORMATION: SDL Pp99 probe 2

<400> SEQUENCE: 17

```
ttaatttgtg gctctgacca gttgttcagt cttaaaaagg agccaaaaaa aaaaaa      56
```

<210> SEQ ID NO 18
<211> LENGTH: 58
<212> TYPE: DNA
<213> ORGANISM: Artificial
<220> FEATURE:
<223> OTHER INFORMATION: SDL Pp99 wild type sample

<400> SEQUENCE: 18

```
aaaaaaaaag gtcagagcca caaattaaca tatcataaaa aacaaggaa aaaaaaaa     58
```

<210> SEQ ID NO 19
<211> LENGTH: 58
<212> TYPE: DNA
<213> ORGANISM: Artificial
<220> FEATURE:
<223> OTHER INFORMATION: SDL Pp99 mutant type sample

<400> SEQUENCE: 19

```
aaaaaaaaag gtcagagcca caaattaaga tatcataaaa aacaaggaa aaaaaaaa     58
```

<210> SEQ ID NO 20
<211> LENGTH: 33
<212> TYPE: DNA
<213> ORGANISM: Artificial
<220> FEATURE:
<223> OTHER INFORMATION: SDL Pp99 capture probe

<400> SEQUENCE: 20

```
aaaaaaaaaa aatcctttgt tttttatgat ctg                               33
```

<210> SEQ ID NO 21
<211> LENGTH: 25
<212> TYPE: DNA
<213> ORGANISM: Artificial
<220> FEATURE:
<223> OTHER INFORMATION: universal F primer

<400> SEQUENCE: 21

```
tgtctattgt ttgtgtgctt gtttt                                        25
```

<210> SEQ ID NO 22
<211> LENGTH: 25
<212> TYPE: DNA
<213> ORGANISM: Artificial
<220> FEATURE:
<223> OTHER INFORMATION: universal R primer

<400> SEQUENCE: 22

```
gtgaaaaatc caaataacct tgatg                                        25
```

<210> SEQ ID NO 23
<211> LENGTH: 44
<212> TYPE: DNA
<213> ORGANISM: Artificial

```
<220> FEATURE:
<223> OTHER INFORMATION: probe 3

<400> SEQUENCE: 23
gtgaaaaatc caaataacct tgatgggctc cttttttaaga ctga                44
```